March 19, 1974 W. E. LAMMERTS Plant Pat. 3,525
ROSE PLANT
Filed Nov. 17, 1972
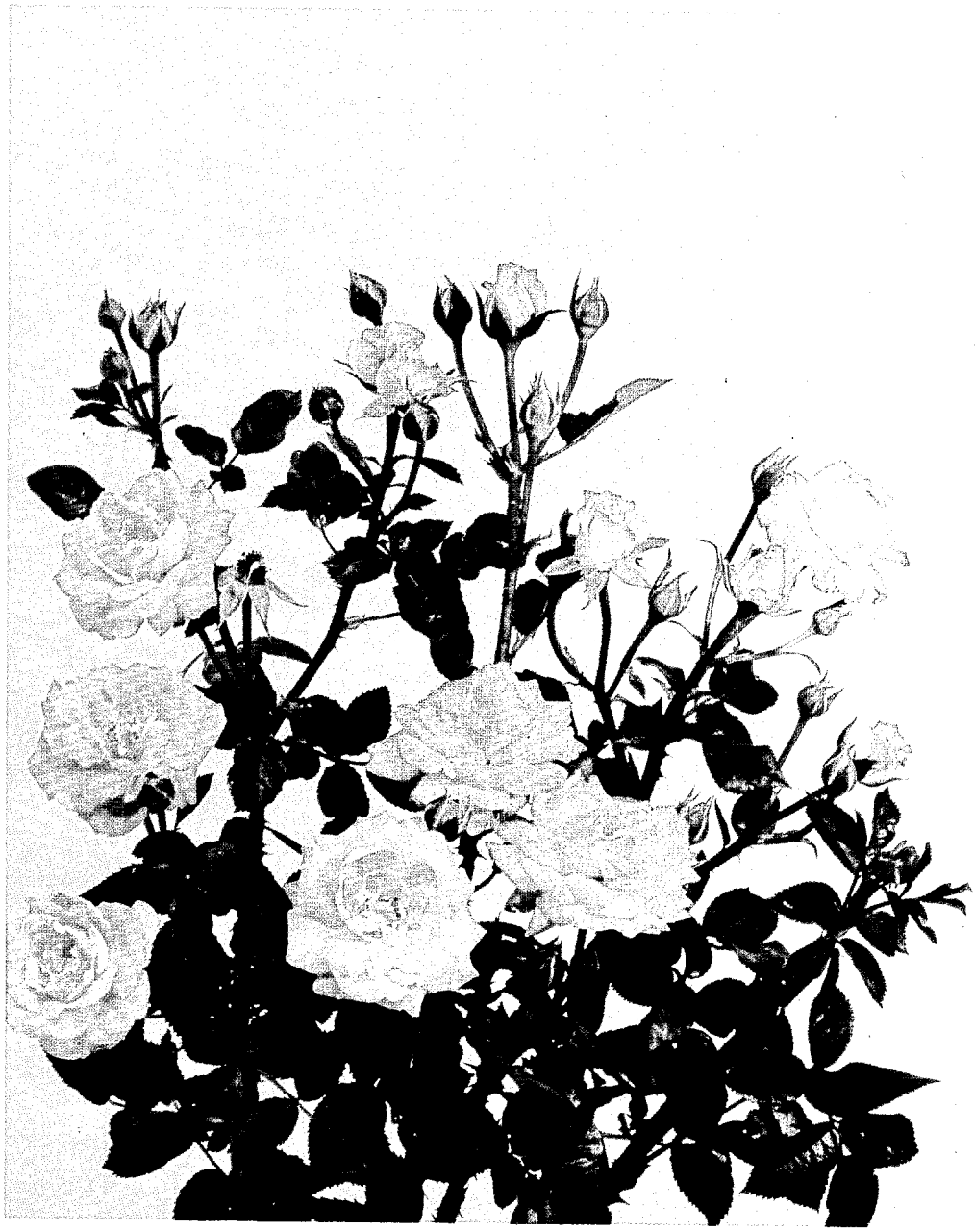

United States Patent Office

Plant Pat. 3,525

Patented Mar. 19, 1974

3,525
ROSE PLANT

Walter E. Lammerts, Watsonville, Calif., assignor to Armstrong Nurseries, Inc., Ontario, Calif.

Filed Nov. 17, 1972, Ser. No. 307,425
Int. Cl. A01h 5/00
U.S. Cl. Plt.—22 1 Claim

ABSTRACT OF THE DISCLOSURE

A small, bushy, upright-spreading rose plant of the floribunda class, having a vigorous habit of growth and producing, practically throughout the season, very numerous blooms of bright pinkish-orange color, these being borne in irregular clusters of usually three or more to a stem. The blooms have a moderate spicy fragrance and range from 2¼" to 2⅝" in diameter. They average about 85 pistils, with 20 to 30 petals and 10 to 18 petaloids. The foliage, which is abundant, is dark green and semi-glossy. It has more than average resistance to mildew.

This invention relates to a new rose plant of the floribunda class. The plant is a seedling of the outdoor bush type, cultivated primarily for garden decoration. It was propagated by Walter E. Lammerts, at Livermore, Calif., and grown at Ontario, Calif.

Its seed parent was "Rumba" (Plant Pat. No. 1,919) and its pollen parent "Tropicana" (Plant Pat. No. 1,969). It holds its distinguishing characteristics through succeeding propagations by budding. Its hardiness has not yet been determined.

The new cultivar bears some flowers singly, but usually three or more to the stem in irregular clusters on strong short to medium-length stems. It blooms abundantly outdoors almost continuously during the growing season. The flowers have a moderate spicy fragrance.

Among the differences between this new variety of rose plant and its seed parent Rumba the following may be noted:

The flower color of this new cultivar is pinkish-orange; while that of Rumba is "poppy red with a yellow center" according to Modern Roses. The new cultivar has significantly more large and small prickles than does Rumba, and the size of its flowers is slightly larger. The new cultivar bears flowers sometimes singly, but usually three or more to the stem; whereas the seed parent Rumba more frequently has more than three flowers in a cluster. The average number of pistils in the new flower is 85; whereas with Rumba it is about 45.

Among the differences between this new variety of rose plant and its pollen parent Tropicana, the following may be noted:

The new variety characteristically bears its flowers in clusters and is of the floribunda class; while its pollen parent, Tropicana, characteristically bears its blooms singly and is of the Hybrid Tea class. The new cultivar bears more flowers than its pollen parent Tropicana. The flower size of this new cultivar ranges from 2¼" to 2⅝" in diameter; whereas the flower size for Tropicana is notably much larger, being generally about 5" in diameter. The flower color of the new cultivar is pinkish-orange, a color deeper and more intense than the coral-orange of Tropicana. The fragrance of the new cultivar is moderate and spicy; whereas Tropicana is very fragrant and fruity in character. The plant of the new cultivar has a growth habit which is lower and more compact than the plant of Tropicana.

The accompanying drawing illustrates the plant in color, and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is of average length and average caliper. It is erect, and has numerous stipitate glands and numerous tiny hairs. Its color is near Strong Yellow Green, 5GY6/8, lightly to heavily overlaid with near Dark Red, 2.5R3/7, where exposed to sunlight.

Before the calyx breaks, it is small to medium size, short to medium length, and ovoid. As the calyx breaks, it has a color between Strong Reddish Orange, 7.5R5/13, and Dark Red, 2.5R3/7, the darker color being more prevalent.

The inner surface of the sepals carries a fine, wooly tomentum. Margins of alternate sepals have small foliaceous appendages and numerous stipitate glands; margins of others have a fine, wooly tomentum. The outer surface of the sepals carries numerous stipitate glands and hairs.

As the first petal opens, it is average in size, medium in length, and ovoid to urn-shaped in form. The outside color of the petal is near Brilliant Greenish Yellow, 10Y9/9, at the base, and ranging through near Strong Reddish Orange, 7.5R6/12, to near Dark Red, 2.5R3/7, as the petal received more light while the bud was opening. The petal on the inside had a color at the base near Brilliant Greenish Yellow, 7.5Y9/8, the main petal color being near but more vivid than Strong Reddish Orange, 10R6/12, and sometimes becoming near Strong Red, 5R4/12, irregularly near the margins.

The bud opens up well, and is not retarded, or prevented from opening, by cold, hot, wet, or dry weather.

BLOOM

When fully open, the bloom is from small to average in size for its class, being 2¼" to 2⅝" in diameter. Its petalage is double, with from 20 to 30 petals, plus 10 to 18 petaloids arranged regularly. It is high-centered at first, becoming open to cupped to high-centered. The petals remain cupped at first, with tips reflexed slightly outward, becoming later, at maturity, more loosely cupped, with tips reflexed outward.

PETALS

The petals are of medium thickness, moderately leathery, with inside satiny and outside slightly shiny to satiny. The outside petals are nearly round, and are sometimes notched. The intermediate petals are obovate in form and are sometimes notched. The inside petals are from nearly round to obovate to irregular, and are also sometimes notched. The colors may be modified by being bordered, blotched, shaded and/or washed with other colors.

The description which follows is of a newly opened flower in the month of June, from a rose plant grown outdoors in Ontario, Calif.:

The outside surface of the outside petal was near Brilliant Greenish Yellow, 10Y9/9, at the base, the remainder of the petal being between Deep Yellowish Pink, 5R6/11, and Deep Pink, 2.5R6/11. The inside surface of the outside petal was more vivid than, but ranged between Strong Reddish Orange, 10R6/12, and Vivid Red, 5R5/13, with a portion at the base being near Brilliant Yellow, 5Y9/9.

The outside surface of the intermediate petal was near Brilliant Greenish Yellow, 7.5Y9/8 at the base, blending to near Strong Yellowish Pink, 10R7/9, in the middle of the petal, and becoming near Deep Yellowish Pink, 5R6/11, near the edges. The inside surface of the intermediate petal was near Brilliant Greenish Yellow, 7.5Y9/8, near the base, the remainder being more vivid than, but between Strong Reddish Orange, 10R6/12, and Strong Reddish Orange, 7.5R6/12.

The inner petal was the same coloration as the intermediate petal, both inside and outside.

The description which follows is of a rose that was open for three days in the month of June, having been grown outdoors in Ontario, Calif.:

The outside surface of the outside petal was near Deep Pink, 10RP6/12, with a portion at the base being between off-white and Brilliant Yellow Green, 2.5GY9/8. The inside surface of the outside petal had a main petal coloration between Deep Yellowish Pink, 5R6/11, and Deep Pink, 2.5R6/11, with a portion at the base the same color as the outside surface, at the base.

The outside surface of the inside petal was mainly between Strong Pink, 10RP7/8, and Strong Purplish Pink, 7.5RP7/10. The inside surface of the inside petal ranged from Strong Pink, 2.5R7/8, to a color between Vivid Red, 5R5/13, and Strong Red, 5R4/12. Both the outer and inner surfaces of the inside petal had a portion at the base which was between off-white and Brilliant Yellow, 5Y9/9.

The general color effect of a newly opened flower was near, but significantly more vivid than, Strong Reddish Orange, 10R6/12. After being three days open, the color effect was near, but more vivid than, Vivid Red, 5R5/13.

The petals drop off cleanly, and are not particularly affected by cold, hot, wet, or dry weather. On the bush in the garden, blooms last from 4 to 5 days in the month of June. Cut roses grown outdoors and kept at living-room temperatures last from 4 to 5 days in the month of June.

REPRODUCTIVE ORGANS

Stamens: Stamens are from average to many in number, arranged regularly about the pistils.

Filaments: Filaments are short to medium-length, being from 1/8" to 3/16" in length, and with a color near Vivid Yellow, 5Y8/12. Most are with anthers.

Anthers: The anthers are from small to medium in size, all opening approximately at once. On both the upper and under side, they are near Brilliant Greenish Yellow, 7.5Y9/8, with margins near Strong Orange Yellow, 7.5YR7/11.

Pollen: Pollen is from moderate to abundant, and near Strong Orange Yellow, 7.5YR7/11, in color.

Pistils: Average number is approximately 85.

Styles: Styles are uneven, of average length, thin to average in caliper, and are somewhat loosely bunched.

Stigma: Near Brilliant Yellow, 5Y9/9.

Ovaries: Most of the ovaries are enclosed in the calyx, with some protruding therefrom.

Hips: None available.

Sepals: None available because no hips were available.

Seeds: None available.

FOLIAGE

Leaves are compound, usually having from 3 to 7 leaflets. They are abundant, medium in size, somewhat leathery, and semi-glossy. Leaflets are ovate in form, with apex mucronate, base obtuse, and margin doubly serrate.

The color of the mature foliage on its upper surface is between Grayish Olive Green, 5GY3/2, and Moderate Olive Green, 5GY4/3. The under surface of the mature foliage is grayer than a color somewhere between Moderate Yellow Green, 7.5GY5/7, and Strong Yellow Green, 7.5GY6/8.

The color of the young foliage on both the upper and lower surface is near Moderate Yellow Green, 5GY5/6, overlaid lightly to heavily with near Dark Red, 2.5R3/7.

The rachis is average in size. Its upper side is grooved, with many stipitate glands on the edges, while the under side is sparsely prickly, and also with stipitate glands.

The stipules are short to medium-length, medium-width to wide, and with medium-length points turning out at an angle of usually less than 45°, recurved slightly toward the stem.

The plant exhibits more than average resistance to mildew, when compared to other varieties now in commerce.

GROWTH

In growth habit, the plant is small, bushy, upright-spreading, and much branched. Its growth is moderately vigorous. Its canes are of medium caliper.

The main stems are of a color between Light Olive, 7.5Y5/5, and Light Olive, 10Y5/5. There are from several to many large prickles which are medium-length, hooked slightly downward, with medium-length, moderately narrow base, these being between gray and Strong Brown, 10YR4/5. There are from few to several small prickles, and their coloration is the same as that of the large prickles. There are no hairs.

The branches are between Strong Yellow Green, 7.5GY6/8, and Moderate Yellow Green, 7.5GY5/7, sometimes being more gray than either of these two colors. There are several large prickles which are medium-length, hooked slightly downward, with medium-length, moderately narrow base. There are from few to many small prickles, and both large and small prickles have a color between Strong Yellow Green, 5GY6/8, and Deep Yellow, 2.5GY6/8, lightly to moderately overlaid with near Moderate Red, 2.5R4/10. There are no hairs, but from few to several stipitate glands.

The new shoots are between Brilliant Yellow Green, 5GY8/8, and Strong Yellow Green, 5GY7/10, lightly to heavily overlaid with near Deep Purplish Red, 10RP3/10. There are a few large prickles which are medium-length, almost straight to hooked slightly downward, with moderately short to medium-length moderately narrow base. There are from several to many small prickles, and both the large and small prickles are near Deep Purplish Red, 10RP3/10. There are from few to several hairs, and from several to many stipitate glands.

I claim:

1. A small bushy rose plant of the floribunda class, substantially as herein illustrated and described, the same being distinguished by a plurality of the following features, in combination: its upright-spreading habit of growth, with abundant dark green semi-glossy foliage, and bearing, practically throughout the growing season, numerous blooms of bright pinkish-orange color, with moderate spicy fragrance, borne usually three or more to a stem, said blooms ranging from 2¼" to 2⅝" in diameter and averaging about 85 pistils, with 20 to 30 petals and 10 to 18 petaloids, said plant having somewhat greater than average resistance to mildew.

No references cited.

ROBERT E. BAGWILL, Primary Examiner